United States Patent
Roso et al.

(10) Patent No.: US 8,119,582 B2
(45) Date of Patent: *Feb. 21, 2012

(54) METHOD FOR IMPROVING THE FOAMING PROPERTIES OF CLEANSING AND/OR FOAMING FORMULATIONS FOR TOPICAL USE

(75) Inventors: Alicia Roso, Saix (FR); Corinne Stoltz, Thiasis (FR)

(73) Assignee: Societe d'Exploitation de Produits pour les Industries Chimiques SEPPIC, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/025,383

(22) Filed: Feb. 11, 2011

(65) Prior Publication Data

US 2011/0136716 A1     Jun. 9, 2011

Related U.S. Application Data

(62) Division of application No. 12/298,862, filed as application No. PCT/FR2007/051119 on Apr. 16, 2007, now Pat. No. 7,915,208.

(30) Foreign Application Priority Data

Apr. 28, 2006 (FR) .................................. 06 51519

(51) Int. Cl.
*A61K 8/60* (2006.01)
(52) U.S. Cl. ...... 510/130; 510/129; 510/136; 424/70.13
(58) Field of Classification Search .................. 510/130, 510/129, 136; 424/70.13
See application file for complete search history.

(56) References Cited

U.S. PATENT DOCUMENTS

| 5,507,970 A | 4/1996 | Ishikawa |
| 6,864,314 B1 * | 3/2005 | Yeung et al. ..................... 525/91 |
| 7,902,135 B2 * | 3/2011 | Roso et al. ..................... 510/130 |
| 7,915,208 B2 * | 3/2011 | Roso et al. ..................... 510/130 |
| 2002/0164115 A1 | 11/2002 | Watanabe |
| 2004/0241127 A1 | 12/2004 | Rose et al. |
| 2005/0069512 A1 | 3/2005 | Rose et al. |
| 2006/0088491 A1 | 4/2006 | Stoltz et al. |
| 2009/0258808 A1 | 10/2009 | Roso et al. |

FOREIGN PATENT DOCUMENTS

| DE | 4439091 | | 5/1996 |
| FR | 1 576 613 | | 8/1969 |
| WO | WO 86/01512 | * | 3/1986 |
| WO | 03094864 | | 11/2003 |

OTHER PUBLICATIONS

International Search Report dated Sep. 6, 2007, filed in PCT application.

* cited by examiner

*Primary Examiner* — Douglas McGinty
(74) *Attorney, Agent, or Firm* — Young & Thompson

(57) ABSTRACT

Methods for improving the foaming properties of cleansing and foaming formulations for topical use are presented. The methods comprise including in the formulation an effective amount of a polyol glycoside or a mixture of polyol glycosides of formula (I) $R_1$—O—$(G)_x$-H, in which x is a decimal number between 1 and 5, G is a reducing sugar and $R_1$ is a radical of formula (A) —$CH_2$—$(CHOH)_n$—$CH_2$—OH, in which n is an integer equal to 2, 3 or 4, or $R_1$ is a radical of the formula (B) —$(CH_2$—CHOH—$CH_2$—O$)_m$—H, in which m is an integer equal to 1, 2 or 3. Compositions containing compounds of formula (I) and methods of preparing the compositions are also presented. The methods and compositions can be applied to cosmetics and dermapharmaceuticals.

15 Claims, No Drawings

METHOD FOR IMPROVING THE FOAMING PROPERTIES OF CLEANSING AND/OR FOAMING FORMULATIONS FOR TOPICAL USE

This application is a divisional application of application Ser. No. 12/298,862 filed Oct. 28, 2008, now U.S. Pat. No. 7,915,208, which is a 371 National Stage application of PCT/FR07/51119 filed Apr. 16, 2007, which claims priority to French Application No. 06 51519 filed on Apr. 28, 2006. The entire contents of each of the above-identified applications are hereby incorporated by reference.

FIELD OF THE INVENTION

The present invention relates to a novel process for improving the foaming properties of cleansing and/or foaming formulations, to novel compositions and to processes for preparing them, and also to the preparation of formulations for topical use containing them.

The invention preferentially finds application in the cosmetic and dermocosmetic fields, in the dermopharmaceutical and pharmaceutical fields, but also in the field of the textile industry, for example for treating synthetic or natural, woven or knitted textile fibers, or alternatively in the field of the paper industry, for example for the manufacture of paper for sanitary or domestic use.

BACKGROUND OF THE INVENTION

The development of cleansing formulations for the face, the body and the hair, and in general body and hair hygiene products, presented in the form of shampoos, lotions, gels or liquid soaps requires the formation of foam during application to the part of the body to be cleansed. This concern is particularly important since, in the eyes of the consumer, the creation of foam constitutes one of the proofs of the cleansing efficacy of these formulations. In the development of cleansing formulations for body and hair hygiene, the volume of foam generated by the formulation, and also its stability and the sensory properties of said foam, constitute an important criterion for the commercial success of the products proposed to consumers. Thus, the search for formulations that generate a foam of good quality is also broadened to all washing products for the body, shower gels and bubble baths.

Several categories of surfactant are used for the preparation of formulations for cleansing purposes: cationic, anionic, amphoteric or nonionic surfactants.

Anionic surfactants, such as sulfated anionic surfactants or surfactants of the alkylcarboxylate family, constitute a class of surfactants that is frequently used on account of their good foaming properties. These surfactants are reputed for their good cleansing power, and may also produce an airy foam whose feel is not considered by consumers to be unpleasant. However, these surfactants have the drawback of being sensitive to the degree of water hardness and to the presence of greasy soiling, which consequently induces a reduction in the volume of foam initially generated by these formulations, but above all a reduction in the stability over time of this volume of foam.

To reduce the magnitude of these phenomena, without, however, eliminating them altogether, it is preferred to use alkyl ether sulfates rather than alkyl sulfates. Another solution, which again is only partially satisfactory, consists in using nonionic surfactants, such as alkylpolyglycosides, for instance decyl polyglucoside or capryl/caprylyl polyglucoside. On account of their nonionic structure, these surfactants are compatible with any other type of surfactant, of additive and of active agent with cosmetic properties, irrespective of their anionic, cationic or nonionic nature. They especially show excellent compatibility with the quaternary ammonium derivatives used either for their bactericidal properties, or for their hair-conditioning effect. Furthermore, alkylpolyglycosides are known for their excellent capacity to form an abundant, stable foam, independently of the pH of the formulation, which foam is insensitive to the degree of water hardness and to the presence of greasy soiling. However, alkylpolyglycosides produce a foam that has mediocre sensory characteristics, reflected by a coarse foam feel, which induces during the rinsing phase a grating effect that consumers find particularly unpleasant, both on the skin and on the hair.

To attempt to overcome these drawbacks, it is necessary either to use a small dose of alkylpolyglycosides in the cleansing formulations, or to combine the alkylpolyglycosides with feel modifiers, for instance water-soluble fatty phases such as silicone fatty phases or esters. Although such combinations make it possible to improve the sensory properties of the foam, they however have the consequence of very significantly reducing the volume of foam formed during use by the consumer, and, in certain cases, of impairing the foam stability over time.

The inventors have thus sought to develop a novel solution for improving the foaming properties of cosmetic, dermocosmetic, dermopharmaceutical or pharmaceutical formulations.

BRIEF DESCRIPTION OF THE INVENTION

Consequently, according to a first aspect, a subject of the invention is a process for improving the foaming properties of a cleansing and/or detergent formulation for topical use, characterized in that an effective amount of a compound of formula (I):

$$R_1\text{—O-}(G)_x\text{-H} \qquad (I)$$

in which:

x represents a decimal number between 1 and 5,

G represents a reducing sugar residue, and $R_1$ represents a monovalent radical of formula (A):

$$\text{—CH}_2\text{—(CHOH)}_n\text{—CH}_2\text{—OH} \qquad (A)$$

in which n is an integer equal to 2, 3 or 4, or alternatively $R_1$ represents a monovalent radical of formula (B):

$$\text{—(CH}_2\text{—CHOH—CH}_2\text{—O)}_m\text{H} \qquad (B)$$

in which m is an integer equal to 1, 2 or 3, or a mixture of compounds of formula (I), is incorporated into said composition.

DETAILED DESCRIPTION OF THE INVENTION

In the definition of formula (I) as defined previously, x is a decimal number that represents the mean degree of polymerization of the residue G. When x is an integer, (G)x is the polymer residue of rank x of the residue G. When x is a decimal number, formula (I) represents a mixture of compounds:

$$a_1R_1\text{—O-G-H}+a_2R_1\text{—O-}(G)_2\text{-H}+a_3R_1\text{—O-}(G)_3\text{-H}+\ldots+a_q$$

$R_1$—O-$(G)_q$-H with q representing an integer between 1 and 10 and in the mole proportions $a_1, a_2, a_3, \ldots a_q$ such that:

$$\sum_{q=10}^{q-1} a_q = 1;$$

$$a_1 > 0$$

According to another particular aspect of the present invention, in the definition of the compounds of formula (I), x is between 1.05 and 5, and more particularly between 1.05 and 2.

The term "effective amount" denotes, in the definition of the process as defined above, an amount such that the final formulation obtained by said process:
  generates a volume of foam of greater than or equal to 300 cm³, 30 seconds after its formation, according to the operating conditions of the Ross-Miles test derived from standard ISO 696 and AFNOR NFT 73-404, the protocol of which is described in paragraph B.1.2 of the experimental section of the present description;
  shows a foam stability of greater than 90%, 5 minutes after its formation, according to the operating conditions of the Ross-Miles test.

According to one particular mode of the process as defined above, the term "effective amount of compound of formula (I)" denotes a mass proportion of from 0.1% to 20%, most particularly from 0.5% to 10% and even more particularly from 1% to 5% of the final formulation.

The term "for topical use" used in the definition of the process as defined above means that said composition is used by application to the skin, the hair, the scalp or mucous membranes, whether it is a matter of a direct application in the case of a cosmetic, dermocosmetic, dermopharmaceutical or pharmaceutical composition, or of an indirect application, for example in the case of a body hygiene product in the form of a textile or paper wipe or of sanitary products intended to come into contact with the skin or mucous membranes.

The term "reducing sugar" denotes, in the definition of formula (I) of the compound used in the process as defined above, saccharide derivatives that do not have in their structure a glycoside bond established between an anomeric carbon and the oxygen of an acetal group, as defined in the reference text: "Biochemistry", Daniel Voet/Judith G. Voet, p. 250, John Wiley & Sons, 1990.

The oligomeric structure $(G)_x$ may be in any isomeric form, whether it is optical isomerism, geometrical isomerism or positional isomerism; it may also represent a mixture of isomers.

In formula (I) as defined above, the group $R_1$—O— is bonded to G via the anomeric carbon of the saccharide residue, so as to form an acetal function.

According to another particular aspect of the process as defined above, in formula (I), G represents a reducing sugar residue chosen from glucose, dextrose, sucrose, fructose, idose, gulose, galactose, maltose, isomaltose, maltotriose, lactose, cellobiose, mannose, ribose, xylose, arabinose, lyxose, allose, altrose, dextran and talose, and more particularly a reducing sugar chosen from glucose, xylose and arabinose.

According to one particular aspect of the present invention, one subject thereof is a process as defined previously, in which the cleansing and/or detergent formulation for topical use comprises at least one foaming and/or detergent surfactant.

The term "foaming and/or detergent surfactant" denotes the topically acceptable anionic, cationic, amphoteric or nonionic surfactants usually used in this field of activity.

Among the anionic surfactants that may be combined with these compounds and with these formulations, mention will be made particularly of alkali metal salts, alkaline-earth metal salts, ammonium salts, amine salts and amino alcohol salts of the following compounds: alkyl ether sulfates, alkyl sulfates, alkylamido ether sulfates, alkylaryl polyether sulfates, monoglyceride sulfates, α-olefin sulfonates, paraffin sulfonates, alkyl phosphates, alkyl ether phosphates, alkylsulfonates, alkylamidesulfonates, alkylaryl-sulfonates, alkylcarboxylates, alkylsulfosuccinates, alkyl ether sulfosuccinates, alkylamide sulfosuccinates, alkylsulfoacetates, alkylsarcosinates, acylisethionates, N-acyltaurates and acyllactylates. Among the anionic surfactants, mention will also be made of lipoamino acids, lipoproteins, lipopeptides, lipoprotein derivatives, protein derivatives, fatty acid salts, and salts of optionally hydrogenated coconut oil acids.

Among the amphoteric surfactants that may be combined with these compounds and with these formulations, mention will be made particularly of alkylbetaines, alkylamidobetaines, sultaines, alkylamidoalkylsulfo-betaines, imidazoline derivatives, phosphobetaines, amphopolyacetates and amphopropionates.

Among the cationic surfactants that may be combined with these compounds and with these formulations, mention will be made particularly of quaternary ammonium derivatives.

Among the nonionic surfactants that may be combined with these compounds and with these formulations, mention will be made particularly of alkylpolyglycosides, castor oil derivatives, polysorbates, coconut amides, N-alkylamines and amine oxides.

Among the foaming and/or detergent surfactants mentioned above, which are anionic surfactants, there are more particularly the compounds of formula (II):

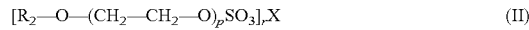

$[R_2—O—(CH_2—CH_2—O)_pSO_3]_rX$      (II)

in which:
  $R_2$ represents a saturated or unsaturated, linear or branched aliphatic hydrocarbon-based radical containing from 6 to 22 carbon atoms,
  represents a decimal number between 1 and 10 and preferably between 2 and 4,
  r is an integer equal to 1 or 2, and
  X represents the cation of an alkali metal or of an alkaline-earth metal, the ammonium ion, the hydroxyethylammonium ion or the tris(hydroxyethyl)-ammonium ion.

In formula (II) as defined above, X represents, for example, sodium, magnesium or ammonium.

Among the foaming and/or detergent surfactants mentioned above, which are nonionic surfactants, there are more particularly the compounds of formula (III):

$R_3—O—(S)_y—H$      (III)

in which:
  y represents a decimal number between 1 and 5,
  S represents a reducing sugar residue, and
  $R_3$ represents a linear or branched, saturated or unsaturated alkyl radical containing from 8 to 16 carbon atoms and preferably from 8 to 14 carbon atoms.

In the definition of formula (III) as defined previously, y is a decimal number that represents the mean degree of polymerization of the residue S. When y is an integer, $(S)_y$ is the polymer residue of rank y of the residue S; when y is a decimal number, formula (III) represents a mixture of compounds:

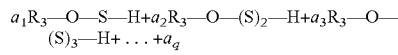

$a_1R_3$—O—S—H+$a_2R_3$—O—$(S)_2$—H+$a_3R_3$—O—$(S)_3$—H+ . . . +$a_q$ $R_3$—O—$(S)_q$—H with q representing an integer between 1 and 10 and in the mole proportions $a_1, a_2, a_3, \ldots a_q$ such that:

$$\sum_{q=10}^{q-1} a_q = 1;$$

$$a_1 > 0$$

According to another particular aspect of the present invention, in the definition of the compounds of formula (III), y is between 1.05 and 5 and more particularly between 1.05 and 2.

In formula (III) as defined above, $R_3$ represents, for example, an n-octyl radical, an n-decyl radical, an n-dodecyl radical or an n-tetradecyl radical.

The term "reducing sugar" denotes, in the definition of formula (III) of the compound used in the process as defined above, saccharide derivatives that do not have in their structure a glycoside bond established between an anomeric carbon and the oxygen of an acetal group, as defined in the reference text: "Biochemistry", Daniel Voet/Judith G. Voet, p. 250, John Wiley & Sons, 1990. The oligomeric structure $(S)_y$ may be in any isomeric form, whether it is optical isomerism, geometrical isomerism or positional isomerism; it may also represent a mixture of isomers.

In formula (III) as defined above, the group $R_3$—O— is bonded to S via the anomeric carbon of the saccharide residue, so as to form an acetal function.

According to another particular aspect of the process as defined previously, the mass ratio of compounds of formula (I) to foaming and/or detergent surfactants present in said composition for topical use is between 1/30 and 10/1 and more particularly between 1/30 and 1/1.

According to a second aspect, a subject of the invention is a composition (C) comprising, per 100% of its mass:

from 97% to 40% by mass of a compound of formula (III):

$$R_3\text{—O—}(S)_y\text{—H} \quad (III)$$

in which:

y represents a decimal number between 1 and 5,

S represents a reducing sugar residue, and $R_3$ represents a linear or branched, saturated or unsaturated alkyl radical containing from 8 to 16 carbon atoms and preferably from 8 to 14 carbon atoms, or a mixture of compounds of formula (III);

from 1% to 25% by mass of a compound of formula (I):

$$R_1\text{—O-}(G)_x\text{-H} \quad (I)$$

in which:

x represents a decimal number between 1 and 5,

G represents a reducing sugar residue, and $R_1$ represents a monovalent radical of formula (A):

$$\text{—CH}_2\text{—(CHOH)}_n\text{—CH}_2\text{—OH} \quad (A)$$

in which n is an integer equal to 2, 3 or 4, or alternatively $R_1$ represents a monovalent radical of formula (B):

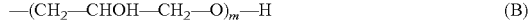

$$\text{—(CH}_2\text{—CHOH—CH}_2\text{—O)}_m\text{—H} \quad (B)$$

in which m is an integer equal to 1, 2 or 3, or a mixture of compounds of formula (I); and up to 50% by mass of a topically acceptable solvent.

In the context of the present invention, the term "topically acceptable solvent" denotes solvents known to those skilled in the art that may be applied to human and/or animal skin, to the scalp and to mucous membranes.

According to a first particular aspect of the composition (C), in formula (I), G represents a reducing sugar residue chosen from glucose, xylose and arabinose.

According to a second particular aspect of composition (C), in formula (I), $R_1$ represents a monovalent radical of formula (A) for which n is equal to 2 or 3, or a monovalent radical of formula (B) for which m is equal to 1 or 2.

According to a third particular aspect of composition (C), in formula (III), S represents a reducing sugar residue chosen from glucose, xylose and arabinose.

According to a fourth particular aspect of composition (C), in formula (III), $R_3$ represents a radical chosen from n-octyl, n-decyl, n-dodecyl, n-tetradecyl and n-hexadecyl radicals.

The topically acceptable solvent is more particularly chosen from one or more components of a group constituted by water, glycols, polyols, alcohols, alkoxylated polyols and glycol ethers.

In the context of the present invention, the topically acceptable solvents are most particularly chosen from one or more components of a group constituted by water, ethanol, isopropanol, butylene glycol, hexylene glycol, caprylyl glycol or 1,2-octanediol, pentylene glycol or 1,2-pentanediol, ethylhexylglycerol or octoxyglycerol, glycerol, diglycerol, triglycerol, erythritol, xylitol, sorbitol, butyldiglycol, polyethylene glycols with a molecular weight of between 200 g·mol$^{-1}$ and 8000 g·mol$^{-1}$, monopropylene glycol, dipropylene glycol, butyldiglycol and 2-methyl-1,3-propanediol.

Advantageously, the abovementioned topically acceptable solvent is chosen from water and one or more components of the group of polyols constituted by xylitol, erythritol, sorbitol, glycerol and diglycerol.

The compounds of formula (III) or the mixtures of compounds of formula (III), the compounds of formula (I) or the mixtures of compounds of formula (I) and the topically acceptable solvent may be incorporated into the cosmetic formulation for topical use separately or in the form of a composition (C) that is the subject of the invention. Moreover, according to one or more routes for preparing the compounds of formula (I) or mixtures of compounds of formula (I), which consists in reacting a reducing sugar G with a polyol of formula (A1):

$$\text{HO—CH}_2\text{—(CHOH)}_n\text{—CH}_2\text{—OH} \quad (A1)$$

in which n is an integer equal to 2, 3 or 4 and/or of formula (B1):

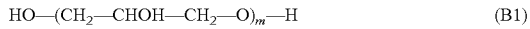

$$\text{HO—(CH}_2\text{—CHOH—CH}_2\text{—O)}_m\text{—H} \quad (B1)$$

in which m is an integer equal to 1, 2 or 3, the amount of unreacted polyol, when this has been selected from one or more components of the group defined previously, may constitute all or part of the topically acceptable solvent. In this case, the compounds of formula (I) or the mixtures of compounds of formula (I) and the topically acceptable solvent are incorporated into the cosmetic formulation for topical use concomitantly and the compounds of formula (III) may be incorporated in a subsequent step.

According to the processes used for preparing composition (C) according to the invention, (C) may residually comprise secondary compounds resulting from the preparation of the compounds of formula (I), for instance the polyols of formula (A1) or the polyols of formula (B1) in their dehydrated forms. Composition (C) cannot comprise more than 10% of these secondary compounds.

Composition (C) that is the subject of the invention may be obtained by various routes:

A first synthetic route consists in a first step (a) in introducing a compound of formula (I) or a mixture of compounds of formula (I) and a compound of formula (III) or a mixture of compounds of formula (III) into a reactor at a controlled mass ratio, and in subjecting this mixture to efficient mechanical stirring, under temperature conditions that ensure the homogeneity of the mixture, preferentially between 20° C. and 90° C. If necessary, a second step (b) consists in introducing a topically acceptable solvent as defined previously into the mixture obtained during step (a), and in continuing the stirring until a homogeneous composition is obtained.

A second synthetic route for composition (C) according to the invention consists in synthesizing during a first step (a1) the compound of formula (I) or the mixture of compounds of formula (I) by introducing a reducing sugar and a polyol of formula (A1) or (B1), for instance erythritol, xylitol, glycerol, diglycerol, triglycerol or sorbitol, into a reactor, at a controlled stoichiometric ratio, and in subjecting this mixture to an acetalization reaction under predetermined temperature and partial vacuum conditions in the presence of an acidic catalytic system. The components of this acidic catalytic system will generally be chosen from sulfuric acid, hydrochloric acid, phosphoric acid, nitric acid, hypophosphorous acid, methanesulfonic acid, para-toluenesulfonic acid, trifluoromethanesulfonic acid and acidic ion-exchange resins. Usually, the acetalization reaction will be performed at a temperature of from 70 to 130° C., under a vacuum of from 300 to $20 \times 10^2$ Pa (300 to 20 m bar). During a second step (b1), a compound of formula (III) or a mixture of compounds of formula (III) is mixed with the reaction product obtained during step (a1), via a stirring system allowing a homogeneous composition to be obtained. If necessary, a third step (c1) consists in introducing a topically acceptable solvent as defined previously to the mixture obtained during step (b1), and in continuing the stirring until a uniform composition is obtained.

A third synthetic route consists in subjecting the polyol of formula (A1) or (B1) to a dehydration, in the presence of an acidic catalytic system, at a temperature of between 70° C. and 130° C., under partial vacuum, with concomitant removal of the water formed during the intramolecular rearrangement that the polyol undergoes during a first step (a2); and then in acetalizing the dehydrated polyol thus obtained by dispersing a reducing sugar in the reaction medium and maintaining this medium at a temperature of between 80° C. and 130° C., under partial vacuum, during a second step (b2). The acidic catalytic system used in this third synthetic route may be identical to that mentioned for the second route. If necessary, a third step (c2) consists in introducing a topically acceptable solvent as defined previously into the mixture obtained during step (b2), and in continuing the stirring until a homogeneous composition is obtained.

A fourth synthetic route via trans-acetalization consists in preparing butylglucoside by reaction between butanol and glucose in the presence of an acidic catalytic system, at a temperature of between 90° C. and 105° C., under partial vacuum, with concomitant removal of the water formed during the reaction during a first step (a3), the acidic catalytic system used possibly being identical to that mentioned for the preceding synthetic routes; adding a polyol of formula (A1) or (B1) to the reaction medium thus obtained, with removal by distillation under vacuum of the residual butanol, of the butanol formed during the trans-acetalization reaction, and of any water generated during the intramolecular rearrangement of said polyol during a second step (b3); and, if necessary, a third step (c3) that consists in introducing a topically acceptable solvent as defined previously into the mixture obtained during step (b3), and in continuing the stirring until a homogeneous composition is obtained.

According to a third aspect, a subject of the invention as defined previously is the use of a compound of formula (I) as defined previously, or of a mixture of compounds of formula (I) or the use of a composition (C) as defined previously, for improving the foaming properties of a cosmetic, dermocosmetic, dermopharmaceutical or pharmaceutical composition for topical use.

According to a fourth aspect, a subject of the invention is the preparation of a cleansing and/or foaming formulation for topical use by using an effective amount of a composition (C) as defined previously. The term "effective amount" denotes a mass proportion of the composition (C) defined previously in the cleansing and/or detergent formulation of between 0.5% and 50%, more particularly between 1% and 30% and most particularly between 2% and 10% of the total mass of said formulation.

The compounds of formula (I), the mixtures of compounds of formula (I) and composition (C) as defined previously may be incorporated into any type of cosmetic, dermocosmetic, dermopharmaceutical or pharmaceutical formulation intended for topical use, or alternatively into any type of support intended to be placed in contact with the skin (paper, wipe, textile, transdermal device, etc.). The cosmetic formulations for topical use in which is incorporated an effective amount of compounds of formula (I) or of mixtures of compounds of formula (I), and which optionally contain one or more foaming and/or detergent surfactants, or alternatively composition (C) defined previously, may be applied, without preference, to the skin, to the hair, to the scalp and to mucous membranes, and may especially be in the form of an aqueous or oily solution, an emulsion or microemulsion of the water-in-oil (W/O) or oil-in-water (O/W) type, a multiple emulsion of water-in-oil-in-water (W/O/W) or oil-in-water-in-oil (O/W/O) type, a gel, a soap or a syndet, a balm, a hydrodispersion, a cream, a mousse or an aerosol, or alternatively in anhydrous form as a powder. These formulations may be used as cleansing or makeup-removing milks, as cleansing or makeup-removing lotions, as foaming gels for the face or the body, as shampoos or hair conditioners, or as bubble baths.

In general, these formulations comprise, in addition to the foaming and/or detergent surfactants that may optionally be present therein, excipients and/or active principles usually used in the field of formulations for topical use, in particular cosmetic, dermocosmetic, pharmaceutical or dermopharmaceutical formulations, thickeners, gelling agents, stabilizers, film-forming compounds, solvents and co-solvents, hydrotropic agents, plasticizers, fats, oils, emulsifiers and co-emulsifiers, opacifiers, nacreous agents, overfatting agents, sequestrants, chelating agents, antioxidants, fragrances, preserving agents, conditioning agents, bleaching agents intended for bleaching bodily hair and the skin, sunscreens, mineral fillers or pigments, particles that afford a visual effect or that are intended for encapsulating active agents, exfoliant particles, texture agents, optical brighteners and insect repellents.

As examples of thickening and/or gelling polymers that may be present in the formulation for which the process that is the subject of the present invention is used, mention may be made of:

homopolymers or copolymers of acrylic acid or of acrylic acid derivatives, acrylamide homopolymers or copolymers, homopolymers or copolymers of acrylamide derivatives, homopolymers or copolymers of acrylamidomethylpropanesulfonic acid, of vinyl monomer and/or of trimethylaminoethyl acrylate chloride sold under the names Carbopol™, Ultrez™ 10, Aculyn™, Pemulen™ TR1, Pemulen™ TR2, Simulgel™ EG, Simulgel™ EPG, Luvigel™ EM, Salcare™ SC91, Salcare™ SC92, Salcare™ SC95, Salcare™ SC96, Flocare™ ET100, Flocare™ ET58, Hispagel™, Sepigel™ 305, Sepigel™ 501, Sepigel™ 502, Simulgel™ NS, Simulgel™ 800, Simulgel™ A, Sepiplus™ 250, Sepiplus™ 265, Sepiplus™ 400, Sepinov™ EMT 10, Novemer™ EC1, Aristoflex™ AVC, Aristoflex™ HBM, Rapithix™ A60, Rapithix™ A100, Cosmedia™ SP and Stabileze™ 06;

hydrocolloids of plant or biosynthetic origin, for example xanthan gum, karaya gum, carrageenates, alginates or galactomannans;

silicates; cellulose and derivatives thereof; starch and hydrophilic derivatives thereof; polyurethanes.

As examples of thickening and/or gelling surfactants that may be present in the formulation for which the process that is the subject of the present invention is used, mention may be made of:

optionally alkoxylated fatty esters of alkylpolyglycosides, and most particularly ethoxylated esters of methylpolyglucoside such as PEG 120 methyl glucose trioleate and PEG 120 methyl glucose dioleate, sold, respectively, under the names Glucamate™ LT and Glumate™ DOE120;

alkoxylated fatty esters such as PEG 150 pentaerythrityl tetrastearate sold under the name Crothix™ DS53 and PEG 55 propylene glycol oleate sold under the name Antil™ 141;

fatty-chain polyalkylene glycol carbamates such as PPG 14 laureth isophoryl dicarbamate sold under the name Elfacos™ T211, and PPG 14 palmeth 60 hexyl dicarbamate sold under the name Elfacos™ GT2125.

As examples of emulsifiers that may be present in the formulation for which the process that is the subject of the present invention is used, mention may be made of:

fatty acids, ethoxylated fatty acids, fatty acid esters of sorbitol, ethoxylated fatty acid esters, polysorbates, polyglyceryl esters, ethoxylated fatty alcohols, sucrose esters, alkylpolyglycosides, sulfated and phosphated fatty alcohols or mixtures of alkylpolyglycosides and of fatty alcohols described in French patent applications 2 668 080, 2 734 496, 2 756 195, 2 762 317, 2 784 680, 2 784 904, 2 791 565, 2 790 977, 2 807 435, 2 804 432, 2 830 774 and 2 830 445, combinations of emulsifying surfactants chosen from alkylpolyglycosides, combinations of alkylpolyglycosides and of fatty alcohols, and polyglycerol or polyglycol or polyol esters such as the polyglycol or polyglycerol polyhydroxystearates used in French patent applications 2 852 257, 2 858 554, 2 820 316 and 2 852 258.

As examples of opacifiers and/or nacreous agents that may be present in the formulation for which the process that is the subject of the present invention is used, mention may be made of sodium or magnesium palmitates, stearates or hydroxystearates, ethylene or polyethylene glycol monostearates or distearates, fatty alcohols, and styrene homopolymers and copolymers such as the styrene acrylate copolymer sold under the name Montopol™ OP1 by the company SEPPIC.

As examples of oils that may be present in the formulation for which the process that is the subject of the present invention is used, mention may be made of:

mineral oils such as liquid paraffin, liquid petroleum jelly, isoparaffins or white mineral oils;

oils of animal origin, such as squalene or squalane, plant oils, such as phytosqualane, sweet almond oil, coconut oil, castor oil, jojoba oil, olive oil, rapeseed oil, groundnut oil, sunflower oil, wheatgerm oil, corn germ oil, soybean oil, cottonseed oil, alfalfa oil, poppy oil, pumpkin oil, evening primrose oil, millet oil, barley oil, rye oil, safflower oil, candlenut oil, passion flower oil, hazelnut oil, palm oil, shea butter, apricot kernel oil, beauty-leaf oil, sysymbrium oil, avocado oil, calendula oil and oils obtained from flowers or vegetables;

ethoxylated plant oils;

synthetic oils, for instance fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, lanolic acid-based esters, such as isopropyl lanolate, isocetyl lanolate, fatty acid monoglycerides, diglycerides and triglycerides, for instance glyceryl triheptanoate, alkyl benzoates, hydrogenated oils, poly-α-olefins, polyolefins, for instance polyisobutene, synthetic isoalkanes such as isohexadecane and isododecane, and perfluoro oils, and silicone oils, for instance dimethylpoly-siloxanes, methylphenylpolysiloxanes, silicones modified with amines, silicones modified with fatty acids, silicones modified with alcohols, silicones modified with alcohols and fatty acids, silicones modified with polyether groups, epoxy-modified silicones, silicones modified with fluoro groups, cyclic silicones and silicones modified with alkyl groups.

As another fatty material that may be present in the formulation for which the process that is the subject of the present invention is used, mention may be made of fatty alcohols or fatty acids; waxes such as beeswax, carnauba wax, candelilla wax, ouricury wax, Japan wax, cork fiber wax, sugarcane wax, paraffin waxes, lignite waxes, microcrystalline waxes, lanolin wax; ozokerite; polyethylene wax, silicone waxes; plant waxes; fatty alcohols and fatty acids that are solid at room temperature; glycerides that are solid at room temperature.

As examples of active principles that may be present in the formulation for which the process that is the subject of the present invention is used, mention may be made of compounds with lightening or depigmenting action, moisturizing action, tensioning action, soothing or relaxing action, anti-inflammatory action, slimming action, lipolytic action, draining action, detoxifying action, energizing action, decontracting action, stimulating action, emollient action, neuromodulatory action, protective action, purifying action, sebum-regulating action, hair-loss-counteracting action, anti-ageing action, firming action, restructuring action, free-radical-scavenging action or antioxidant action; such active principles are, for example, Sepiwhite™ MSH, arbutin, kojic acid, hydroquinone, ellagic acid, vitamin C and its derivatives, Stay C, magnesium ascorbyl phosphate and its derivatives, ascorbyl glucoside, phytic acid, fruit acids, rucinol or resorcinol, azeleic acid, lipoic acid, Vegewhite™, Gatuline™, Synerlight™, Biowhite™, Phytolight™, Dermalight™, Clariskin™, Melaslow™, Dermawhite™, Ethioline™, Melarest™, Gigawhite™, Albatine™, Lumiskin™, polyphenol extracts, grape extracts, pine extracts, wine extracts, olive extracts, pond extracts, N-acyl proteins, N-acyl peptides, for instance Matrixyl™, N-acylamino acids, partial hydrolysates of N-acyl proteins, amino acids, peptides, total protein hydrolysates, polyols (for instance glycerol, butylene glycol, etc.), milk derivatives, or the various components included in the composition of NMF (natural moisturizing factor), for example urea, pyrrolidonecarboxylic acid or derivatives of this acid, amino acids, mineral salts, glucosamines, glycyrrhetinic acid, α-bisabolol, sugars or sugar derivatives, polysaccharides or derivatives thereof, hydroxy acids, for instance lactic acid, vitamins, vitamin derivatives, for instance retinol, vitamin E and its derivatives, trace elements, extracts of rocks or stones, enzymes, coenzymes, for instance coenzyme Q10, hormones or "hormone-like" substances, for instance Phyto Age™, soybean extracts, for instance Raffermine™, wheat extracts, for instance Tensine™ or Gliadine™, plant extracts such as tannin-rich plant extracts, isoflavone-rich plant extracts or terpene-rich plant extracts, freshwater or saltwater algal extracts, marine extracts in general, including coral extracts, essential waxes, bacterial extracts, minerals, for instance the range of Givobio™ products, calcium, magnesium, copper, cobalt, zinc, lithium or manganese derivatives, silver or gold salts, lipids in general, lipids such as ceramides or phospholipids, active agents with slimming or lipolytic action, for instance caffeine or derivatives thereof, calcium and derivatives thereof, and Lipaslim™, active agents that improve the capillary circulation of the skin, for example venotonic agents, water retention-reducing active agents, active agents for decongesting purposes such as ginkgo biloba, ivy, common horse chestnut, bamboo, ruscus, centella asiatica, fucus, rosemary or sage, active agents with antimicrobial activity or a purifying action on greasy skin, for instance Lipacide™ CBG, Lipacide™ UG, Sepicontrol™ A5, copper or zinc derivatives, Octopirox™ or Sensiva™ SC50, active agents with energizing or stimulating properties, for instance Sepitonic™ M3 or Physiogenyl™, panthenol and derivatives thereof, for instance Sepicap™ MP, anti-ageing active agents, for instance Sepilift™ DPHP, Lipacide™ PVB, Sepivinol™, Sepivital™, Manoliva™ and Phyto-Age™, moisturizing active agents, for instance Sepicalm™ S, Sepicalm™ VG and Lipacide™ DPHP, photoageing-counteracting active agents, active agents for protecting the integrity of the dermo-epidermal junction, active agents for increasing the synthesis of components of the extracellular matrix, for example collagen, elastins, glycosaminoglycans, active agents that act favorably on chemical cellular communication, for instance cytokines, or on physical cellular communication, for instance integrins, active agents that create a "heating" sensation on the skin, for instance activators of the capillary circulation of the skin (for example nicotinates) or products that create a sensation of "freshness" on the skin (for example menthol and derivatives thereof).

As sunscreens that may be present in the formulation for which the process that is the subject of the present invention is used, mention may be made of all the agents featured in Cosmetic Directive 76/768/EEC amended appendix VII.

The examples that follow illustrate the invention without, however, limiting it.

A)—Preparation of the Compounds of Formula (I) or of Mixtures of Compounds of Formula (I), and of the Compositions According to the Invention

EXAMPLE 1

Composition (C1) Constituted of Xylitylpolyglucosides, Sodium Lauryl Ether (2.2 EO) Sulfate and Xylitol 703.0 g of xylitol are placed in a jacketed glass reactor, in which circulates a heat-exchange fluid, and which is equipped with an efficient stirrer. The xylitol is melted at a temperature of 135° C. and the viscous paste thus obtained is cooled to 115° C. Glucose is then gradually added to the reaction medium to allow its uniform dispersion. An acidic catalytic system constituted of 1.29 g of 96% sulfuric acid is added to the mixture thus obtained. The reaction medium is placed under a partial vacuum of $90 \times 10^2$ Pa (90 mbar) to $45 \times 10^2$ Pa (45 mbar) and maintained at a temperature of 100° C.-105° C. for a duration of 4 hours 30 minutes, with removal of the water formed by means of distillation apparatus. The reaction medium is then cooled to 95° C.-100° C. and neutralized by adding 5 g of 30% sodium hydroxide, to bring the pH of a 1% solution of this mixture to a value of 5.0. The characteristics of the intermediate mixture thus obtained are as follows:

aspect (visual): orange wax at room temperature;
pH of a 1% solution: 5.0;
residual xylitol: 56 mass %;
residual glucose: <1 mass %;
xylitylpolyglucosides: 38 mass %.

15.86 g of the intermediate mixture obtained previously and 572.9 g of sodium lauryl ether (2.2 EO) sulfate at 28% in water are mixed together at 50° C. in a jacketed glass reactor, in which circulates a heat-exchange fluid, and which is equipped with an efficient stirrer.

After obtaining a homogeneous mixture, composition (C1) comprises, per 100 mass % of its dry matter, 91% sodium lauryl ether (2.2 EO) sulfate, 4% xylitylpolyglucoside and 5% xylitol.

COMPARATIVE EXAMPLE 1

Sodium Lauryl Ether (2.2 EO) Sulfate (T1)

EXAMPLE 2

Composition (C2) Constituted of Xylitylpolyglucosides, n-decyl/n-dodecyl Polyglucosides and Xylitol The xylitylpolyglucosides are prepared according to the process described in Example 1 until an intermediate mixture comprising, per 100% of its mass, 37.2 mass % of xylitylpolyglucosides, 55.8 mass % of xylitol and a mass proportion of residual glucose of less than 1% is obtained. 20 g of the intermediate mixture obtained previously and 113.3 g of a mixture of n-decylpolyglucosides and of n-dodecylpolyglucosides (C10/C12=85/15) as a 55% solution are mixed together at 50° C. in a jacketed glass reactor, in which circulates a heat-exchange fluid, and which is equipped with an efficient stirrer. After obtaining a uniform mixture, composition (C2) comprises, per 100 mass % of its dry matter, 77% n-decylpolyglucosides/n-dodecylpolyglucosides, 9% xylitylpolyglucosides and 14% xylitol.

COMPARATIVE EXAMPLE 2

Composition (T2) Constituted of n-decyl/n-dodecyl Polyglucosides and Xylitol

A 55% solution of n-decylpolyglucosides and of n-dodecylpolyglucosides (C10/C12=85/15) is placed in a beaker at room temperature. The medium is stirred with a magnetic bar coupled to a magnetic stirrer and xylitol is gradually introduced in proportions allowing a composition containing 77 mass % of solids of n-decylpolyglucosides/n-dodecylpolyglucosides and 23 mass % of xylitol to be obtained.

EXAMPLE 3

Composition (C3) Constituted of Xylitylpolyglucosides, n-octyl/n-decyl Polyglucosides and Xylitol The xylitylpolyglucosides are prepared according to the process described in Example 1, until an intermediate mixture comprising, per 100% of its mass, 37.2 mass % of xylitylpolyglucosides, 55.8 mass % of xylitol and a mass proportion of residual glucose of less than 1% is obtained. 20 g of the intermediate mixture obtained previously and 103.8 g of a mixture of n-octylpolyglucosides and of n-decylpolyglucosides (C8/C10=50/50) as a 60% solution are mixed together at 50° C. in a jacketed glass reactor, in which circulates a heat-exchange fluid, and which is equipped with an efficient stirrer. After obtaining a homogeneous mixture, the mass composition of composition (C3) comprises, per 100% of its dry matter, 77% n-octylpolyglucosides/n-decylpolyglucosides, 9% xylitylpolyglucosides and 14% xylitol.

COMPARATIVE EXAMPLE 3

Solution Containing 55% Dry Matter of n-decylpolyglucosides/n-dodecylpolyglucosides (T3)

EXAMPLE 4

Composition (C4) Constituted by Xylitylpolyglucosides, n-octyl/n-decyl Polyglucosides and Xylitol The xylitylpolyglucosides are prepared according to the process described in Example 1, until an intermediate mixture comprising, per 100% of its mass, 37.2 mass % of xylitylpolyglucosides, 55.8 mass % of xylitol and a mass proportion of residual glucose of less than 1% is obtained. 20 g of the intermediate mixture obtained previously and 62.1 g of a mixture of n-octylpolyglucosides and of n-decylpolyglucosides as a 60% solution are mixed together at 50° C. in a jacketed glass reactor, in which circulates a heat-exchange fluid, and which is equipped with an efficient stirrer. After obtaining a homogeneous mixture, composition (C4) comprises, per 100% of its dry matter, 68% n-octylpolyglucosides/n-decylpolyglucosides, 7% xylitylpolyglucosides and 25% xylitol.

COMPARATIVE EXAMPLE 4

Solution Containing 55% Dry Matter of n-octylpolyglucosides/n-decylpolyglucosides (T4)

EXAMPLE 5

Composition (C5) Constituted by Diglyceryl-Polyxylosides, n-octyl/n-decyl Polyglucosides and Diglycerol 650.0 g of diglycerol are placed in a jacketed glass reactor, in which circulates a heat-exchange fluid, and which is equipped with an efficient stirrer. The diglycerol is brought to a temperature of about 100° C. 1117.5 g of xylose are then gradually added to the reaction medium to allow its uniform dispersion. An acidic catalytic system constituted of 0.51 g of 98% sulfuric acid is added to the mixture thus obtained. The reaction medium is placed under a partial vacuum of $30 \times 10^2$ Pa (30 mbar) and maintained at a temperature of 100° C.-105° C. for a duration of 4 hours, with removal of the water formed by means of distillation apparatus. The reaction medium is then cooled to 95° C.-100° C. and neutralized by adding 30% sodium hydroxide, to bring the pH of a 1% solution of this mixture to a value of about 7.0. The characteristics of the intermediate mixture thus obtained are as follows:
- aspect (visual): clear liquid;
- pH of a 1% solution: 6.8;
- residual diglycerol: 68.1%;
- residual xylose: <1%;
- diglycerylpolyxylosides: 27.7%.

20 g of the intermediate mixture obtained previously and 133.3 g of a mixture of n-octylpolyglucosides and n-decylpolyglucosides as a 60% solution are mixed together at 50° C. in a jacketed glass reactor, in which circulates a heat-exchange fluid, and which is equipped with an efficient stirrer. After obtaining a uniform mixture, composition (C5) comprises, per 100% of its dry matter, 80% n-octylpolyglucosides/n-decylpoly-glucosides, 6% diglycerylpolyxylosides and 14% diglycerol.

EXAMPLE 6

Composition (C6) Constituted by Diglycerylpolyglucosides, n-dodecyl/n-tetradecyl/n-hexadecyl Polyglucosides and Diglycerol The process described in Example 5 is performed to prepare the diglycerylpolyglucosides, replacing the xylose with glucose and keeping the same reducing sugar/diglycerol mole ratio equal to 1/5. The characteristics of the intermediate mixture thus obtained are as follows:
- aspect (visual): clear liquid;
- pH of a 1% solution: 6.8;
- residual diglycerol: 67.2%;
- residual glucose: <1%;
- diglycerylpolyglucosides: 24.7%.

20 g of the intermediate mixture obtained previously and 120 g of a mixture of n-decylpolyglucosides, n-dodecylpolyglucosides, n-tetradecylpolyglucosides and n-hexadecylpolyglucosides sold under the name Plantacare™ 1200 UP are mixed together at 50° C. in a jacketed glass reactor, in which circulates a heat-exchange fluid, and which is equipped with an efficient stirrer. After obtaining a uniform mixture, composition (C6) comprises, per 100% of its dry matter, 75% of a mixture of n-decylpolyglucosides, n-dodecylpolyglucosides, n-tetradecylpolyglucosides and n-hexadecylpolyglucosides, 8% diglycerylpolyglucosides and 17% diglycerol.

Summary Table

Table 1 below summarizes the mass compositions, as dry matter, of various compositions prepared and intended to be used in tests of demonstration of the foaming properties.

TABLE 1

| Composition (as mass %) | C1 | T1 | C2 | T2 | C3 | T3 | C4 | T4 | C5 | C6 |
|---|---|---|---|---|---|---|---|---|---|---|
| Sodium lauryl ether (2.2 EO) sulfate | 91 | 100 | 0 | 0 | 0 | 0 | 0 | 0 | 0 | 0 |
| Xylityl polyglucosides | 4 | 0 | 9 | 0 | 9 | 0 | 7 | 0 | 0 | 0 |
| Xylitol | 5 | 0 | 14 | 23 | 14 | 0 | 25 | 0 | 0 | 0 |
| Diglyceryl polyxylosides | 0 | 0 | 0 | 0 | 0 | 0 | 0 | 0 | 6 | 0 |

TABLE 1-continued

| Composition (as mass %) | C1 | T1 | C2 | T2 | C3 | T3 | C4 | T4 | C5 | C6 |
|---|---|---|---|---|---|---|---|---|---|---|
| Diglyceryl polyglucosides | 0 | 0 | 0 | 0 | 0 | 0 | 0 | 0 | 0 | 8 |
| Diglycerol | 0 | 0 | 0 | 0 | 0 | 0 | 0 | 0 | 14 | 17 |
| n-Octyl/n-decyl polyglucosides | 0 | 0 | 0 | 0 | 77 | 0 | 68 | 100 | 80 | 0 |
| n-Decyl/n-dodecyl polyglucosides | 0 | 0 | 77 | 77 | 0 | 100 | 0 | 0 | 0 | 0 |
| n-Decyl/n-dodecyl/n-tetradecyl/n-hexadecyl polyglucosides | 0 | 0 | 0 | 0 | 0 | 0 | 0 | 0 | 0 | 75 |

B—Demonstration of the Foaming Properties of Formulations Comprising Compounds of Formula (I) or Mixtures of Compounds of Formula (I), and of the Compositions (C) According to the Invention The demonstration of the foaming properties of formulations comprising compounds of formula (I) or mixtures of compounds of formula (I), and of the compositions (C) defined previously forming the subject of the invention, may be performed by evaluating the foaming power or by evaluating the sensory characteristics that the foam formed gives to users during the washing or cleansing operation.

B.1—Demonstration of the Foaming Power

B.1.1—Principle of the Ross-Miles Method for Evaluating the Foaming Power

The foaming power is determined according to the Ross-Miles protocol derived from standard ISO 696 and AFNOR NFT 73-404 and described in paragraph B1.2, diluting the cleansing bases and the compositions prepared previously tenfold, so as to represent the real conditions of foam creation during the use of a shampoo, for example.

The tenfold dilution of the compositions and of the formulations to be tested is performed in the presence of 0.25% of a greasy soiling (a reconstituted sebum) with a demineralized water enriched with 3 millimol of calcium ions, which corresponds to the preparation of a water with a calcium hardness of 30° according to standard NFT 73-047.

The method consists in measuring the volume of foam obtained after dropping, from a height of 450 mm, 500 cm$^3$ of a solution of composition or of formulation to be tested, onto a liquid surface of the same solution.

B.1.2—Experimental Protocol a) Preparation of a Stock Solution (S)

A stock solution is prepared for each test. For the surfactant compositions or formulations to be tested, prepare 100 g of a stock solution (S) with a 10% titer of active material or of solids, diluted with demineralized water enriched with 3 mmol of calcium ions, which corresponds to the preparation of a water with a calcium hardness of 30° according to standard NFT 73-047.

b) Preparation of the Soiling

In the case of determining the foam height in the presence of artificial soiling, the amount of soiling (0.25%, i.e. 1.75 g per 700 g of final solution) and the amount of solution S (i.e. 70 g per 700 g of final solution) required to perform the measurements are weighed out beforehand. The mixture is melted on a water bath preheated to 70° C., for 3 minutes, while stirring with a spatula.

c) Preparation of the Test Solution

The premelted mixture [S+soiling] is diluted tenfold with demineralized water enriched with 3 mmol of calcium ions. The service life of the test solutions is a maximum of 1 hour from the moment at which the final dilution was prepared. The final test solution is then preheated on a water bath at 48° C. for a minimum of 1 hour, and then maintained thermostatically for 30 minutes to reach a temperature of 40° C.±1° C.

d) Measurement 50 cm$^3$ of the test solution are placed in a 50 cm$^3$ measuring cylinder, running the liquid down the walls to avoid any formation of foam. A dropping funnel equipped at its end with a steel tip, such that the height between the surface of the solution contained in the measuring cylinder and the end of the steel tip is 450 mm, is placed a fixed height above the measuring cylinder. About 100 cm$^3$ of the test solution are introduced into the dropping funnel, by running down the walls, and the level is adjusted by pouring up to the graduation mark, thus eliminating the air present in the eye of the tap.

500 cm$^3$ of test solution are then introduced into the dropping funnel, by running down the walls. The dropping funnel is placed on its support and the tap is opened so as to allow the solution to flow in a single portion into the measuring cylinder at a maximum flow rate. The tap is closed when the solution reaches the graduation mark, and the chronometer is then simultaneously started. The height of foam immediately formed on starting the chronometer, and then the height of foam at 30 seconds, at 3 minutes and at 5 minutes, are measured in cm. The foam height is measured between the foam/liquid horizontal interface and the base of the foam/air interface.

B.1.3—Expressing the Results

The result of the volume of foam at 30 seconds is expressed in cm$^3$ by multiplying the height measured at 30 seconds in cm by the cross section of the measuring cylinder (30.2 cm$^2$ or 28.3 cm$^2$ depending on the model). The stability of the foam after 5 minutes, measured as a percentage, is calculated according to the formula:

$$[(\text{volume of foam at 30 s} - \text{volume of foam at 5 min})/\text{volume of foam at 30 s}] \times 100.$$

B.1.4—Influence of the Compounds of Formula (I) or of the Mixtures of Compounds of Formula (I) on the Foaming Power of Formulations Comprising Compounds of Formula (II)

B.1.4.1—Results Obtained

TABLE 2 evaluation of the foaming power of a solution containing a compound of formula (II) and a mixture of compounds of formula (I) (composition C1) and of a solution containing a compound of formula (II) (T1).

| Foaming power | (C1) | T1 |
|---|---|---|
| Volume of foam at 30 seconds (cm$^3$) | 350 | 317 |
| Foam stability at 5 minutes (%) | 94% | 83% |

B.1.4.2—Analysis of the Results

The results are considered satisfactory when the test solution shows a volume of foam at 30 seconds of greater than or equal to 300 cm$^3$ and a foam stability at 5 minutes of greater than or equal to 90%. Comparative Example 1 shows that a solution comprising a compound of formula (II), tested under the conditions described above, is characterized by the generation of an abundant foam at 30 seconds (317 cm$^3$) and by a stability of 83% after 5 minutes. Use of the process according to the invention for preparing composition (C1) makes it possible to achieve both a greater volume of foam after seconds and also a substantially greater foam stability at 5 minutes (94% for composition (C1) and 83% for (T1)). Use of the process according to the invention thus makes it possible to improve the foaming power of compounds of formula (II).

B.2—Demonstration of the Sensory Properties

Among the characteristics that will also be taken into consideration for assessing the quality of a foam formed by a foaming surfactant solution, by a foaming composition and by a foaming formulation, are the sensory characteristics that the foam affords to the user, and which concern the assessment of the softness of the foam formed, the capacity to allow easy sliding of the hands during washing (the "slipperiness"), the ease of rinsing after the washing operation, and the stability of the foam on dilution with washing water during this final operation. These characteristics are determined experimentally by a representative panel of duly trained users, according to the protocol detailed in paragraph B.2.2.

B.2.1—Principle of the Method

The sensory properties of the foam generated by the foaming compositions are evaluated during a hand washing operation by a panel of 10 individuals duly trained for this evaluation, who classify on a scale ranging from 0 to 10: the softness index of the foam, which makes it possible to evaluate the softness sensation experienced by the user; the slipperiness index of the foam, which makes it possible to evaluate the ease with which the hands slide over each other during the phase of rubbing of the hands in the washing operation; the stability index of the foam on dilution, which makes it possible to evaluate the stability of the foam contained in the hand after the phase of rubbing the hands followed by the addition of 2 cm$^3$ of water; the rinseability index of the foam, which makes it possible to evaluate the ease of rinsing of the hands with water after the operation of rubbing the hands with the cleansing product in the form of foam.

B.2.2—Experimental Protocol

To take reproducible measurements, the solutions were conditioned in bottles equipped with a metering foam pump, which directly expels the product in the form of foam onto the hands with a fixed amount of test product. The product contained in the bottle is applied directly to one of the hands, which has been moistened beforehand, by pressing twice successively on the foam pump of the bottle. On the moistened hand containing the product from the bottle, the experimenter rubs the other hand out flat for 5 seconds, and then rubs the hands clasped together for a further 5 seconds. The foam is collected together in a single hand to be evaluated by the experimenter, who notes the softness index and the slipperiness index of the foam. 2 cm$^3$ of water are then added from a graduated pipette onto the hand containing the collected foam, and the experimenter notes the stability index of the foam on dilution. The experimenter then rinses his hands under a tap of cold water and evaluates the rinseability of the foam.

B.2.3—Expressing the Results

A softness index of 0 is attributed to a very coarse foam and a softness index of 10 is attributed to a very soft foam. A foam slipperiness index of 0 is attributed to a foam that sticks on the hands and a foam slipperiness index of 10 is attributed to a foam that is very slippery on the hands. A stability index of the foam on dilution of 0 is attributed to a foam that collapses when the 2 cm$^3$ of water are added and a stability index of the foam on dilution of 10 is attributed to a foam that is perfectly maintained when the 2 cm$^3$ of water are added. A rinseability index of 0 is attributed for a hand rinsing considered as being very difficult and a rinseability index of 10 is attributed for a hand rinsing considered as being very easy. For each index, the evaluations made by each of the 10 experimenters are noted and the arithmetic mean of each index is then calculated.

B.2.4—Sensory Properties of the Cleansing and/or Detergent Formulations Obtained by Using the Process According to the Invention and the Compositions According to the Invention

B.2.4.1—Results Obtained

TABLE 3

| Sensory property indices | C1 | T1 | C2 | T2 | T3 | C3 | C4 | T4 |
|---|---|---|---|---|---|---|---|---|
| evaluation of the sensory properties | | | | | | | | |
| Softness | 8 | 7 | 7.7 | 5.2 | 4.0 | 5.5 | 6.0 | 3.0 |
| Slipperiness | 6 | 5.5 | 7.4 | 4.0 | 3.4 | 5.5 | 6.5 | 3.0 |
| Foam stability after dilution | 5 | 3 | 6.8 | 5.5 | 4.5 | 5.4 | 6.0 | 4.0 |
| Rinseability | 5.1 | 5.3 | 6.7 | 6.0 | 7.3 | 6.9 | 7.0 | 7.1 |

B.2.4.2—Analysis of the Results

The results are considered as being satisfactory when one or more of the sensory property indices for the test formulation or the test composition shows a significant improvement, without significantly reducing one or more of the other indices; said indices taken individually should show a value of greater than or equal to 5.0. They reveal an improvement in one or other of the sensory properties induced by the compositions according to the invention compared with those of the prior art.

C)—Formulations

In the following formulations, the percentages are expressed by weight of the formulation.

C.1 Foaming Facial Gel

Formula

| A | 28% sodium lauryl ether (2.2 EO) sulfate | 5.9% |
|---|---|---|
|   | Water | qs 100% |
| B | Composition (C5) according to the invention | 5.0% |
|   | Montaline ™ C40 | 5.0% |
|   | Sepitonic ™ M³ | 1.0% |
|   | Fragrance | 0.1% |
|   | Kathon ™ CG | 0.08% |
| C | Lactic acid | 0.15% |
|   | Sodium chloride | 0.8% |
| D | Dye | 0.05% |
| E | Sodium chloride | qs |

Procedure

Prepare phase A in a fume cupboard. Mix together the ingredients of phase B, homogenizing after each addition. Next, pour A into B. Add C and then D. Adjust the viscosity if necessary by adding E (1.5% max.).

C.2 Bubble Bath for Children

Formula

| A | Oronal ™ LCG | 10.00% |
|---|---|---|
|   | Composition (C2) according to the invention | 13.00% |
|   | Fragrance | 00.10% |
|   | Sepicide ™ HB | 00.50% |
| B | Water | 20.00% |
|   | Capigel ™ 98 | 04.50% |
| C | Water | qs 100% |
|   | Sepicide ™ CI | 00.30% |
|   | Dye | qs |
|   | Sodium hydroxide | qs |

Procedure

Mix the Oronal™ LCG with the amphoteric surfactant, the fragrance and the preserving agent. Dilute the Capigel™ in a portion of water and add it to the surfactants, then add the rest of the water. Add the Sepicide™ CI and the dye, and then adjust the pH to about 7.2.

C.3 Liquid Soap for the Hands

Formula

| A | Composition (C1) | 10.00% |
|---|---|---|
|   | Amonyl ™ 675SB | 10.00% |
|   | Fragrance | 00.30% |
|   | Sepicide ™ HB | 00.50% |
| B | Water | qs 100% |
|   | Sepicide ™ CI | 00.30% |
|   | Sodium chloride | qs |

Procedure

Mix together the ingredients of phase A and then add phase B.

C.4 Concentrated Purifying Lotion

Formula

| A | Water | 20.00% |
|---|---|---|
|   | Lipacide ™ UGB | 1.00% |
|   | Tromethamine | 0.75% |
| B | PEG 120 methyl glucose dioleate | 5.00% |
|   | Water | qs 100% |
|   | Composition (C6) according to the invention | 29.00% |
|   | Glycerol | 5.00% |
| C | Lactic acid | qs pH 4 |

Procedure

Dissolve the Lipacide™ UGB in part of the water heated to 80° C. and then add the tromethamine: this phase should be totally clear. Melt the PEG 120 methyl glucose dioleate in the rest of the water preheated to 80° C. Add to this phase the glycerol and the composition of the invention: this phase is also totally clear. Mix together the two phases, allow to cool and readjust the pH to the desired value.

C.5 Cleansing Facial Foam

Formula

| A | Proteol ™ Oat | 30% |
|---|---|---|
|   | Composition (C3) according to the invention | 10.00% |
|   | Sepicide ™ HB | 00.50% |
|   | Fragrance | 00.20% |
| B | Water | qs 100% |
|   | Sepicide ™ CI | 00.30% |
|   | Sepitonic ™ M3 | 01.00% |
|   | Tromethamine | qs |
|   | Dye | qs |

Procedure

Dissolve the fragrance and the preserving agent in the mixture of surfactants (A). Add the water and then the other ingredients successively.

C.6 Anti-Stress Shampoo

Formula

| A | Composition (C1) | 20.00% |
|---|---|---|
|   | Sepicide ™ HB | 0.50% |
|   | Sepicide ™ CI | 0.30% |
|   | Fragrance | 0.30% |
|   | Water | qs 100% |
|   | Sepicap ™ MP | 1.00% |
| B | Water | 10.00% |
|   | Capigel ™ 98 | 3.00% |
|   | Sodium hydroxide | qs pH 7.2 |
|   | Dye | qs |

Procedure

Mix together the ingredients A and then add the prediluted Capigel. Neutralize.

C.7 Cleansing Wipes

Formula

| A | Composition (C6) | 02.00% |
|---|---|---|
|   | Aquaxyl ™ | 01.00% |
| B | Sepicide ™ HB$_2$ | 00.50% |
|   | Fragrance | 00.05% |
|   | Hexylene glycol | 10.00% |
| C | Water | qs 100% |

Procedure

Mix together the ingredients of phase B until clear and then add this phase to phase A. Add C.

C.8 Relaxing Bath Oil

Formula

| Cedar wood extract | 10.00% |
|---|---|
| Composition (C5) | 66.00% |
| Glycerol | 24.00% |

Procedure

Mix together the essential oil and the composition of the invention until clear. Next, add the glycerol.

C.9 Gentle Cleansing Product with Jojoba Oil

| A | Montanov ™ S | 3.0% |
|---|---|---|
|   | PEG-120 methyl glucose dioleate | 2.0% |
| B | Jojoba oil | 0.5% |
|   | Dimethicone and laureth-23 and laureth-4 and salicylic acid | 2.0% |
| C | Water | 30.0% |
|   | Glycerol | 3.0% |
|   | Polyquaternium ™ 10 | 0.7% |
| D | Somepon ™ T25 | 4.5% |
|   | Composition (C6) | 30.0% |
|   | Water | 5.0% |
|   | Sepicide ™ CI | 0.2% |
|   | Sepicide ™ HB | 0.3% |
|   | Fragrance | 0.1% |
| E | Water | qs 100% |
|   | Capigel ™ 98 | 2.0% |
|   | Sodium hydroxide | qs pH 7 |

Procedure

Disperse the Polyquaternium™ 10 of phase C in the water+glycerol mixture. Heat to 70° C. and add the ingredients of A and then of B. Emulsify. Start cooling. At 60° C., add the surfactants one by one (D). At 30° C., add the prediluted Capigel™ (E). Finally, neutralize with sodium hydroxide.

C.10 Antibacterial Liquid Soap

| Composition (C6) | 15.00% |
|---|---|
| Chlorhexidine digluconate | 00.20% |
| Oramide ™ DL 200 AF | 03.00% |
| Water | qs 100% |
| Fragrance | 00.05% |
| Dye | qs |
| Sodium chloride | qs |

Procedure

Add together and mix the constituents in the indicated order.

C.11 Conditioning Shampoo

| A | Cetyltrimethylammonium chloride | 03.50% |
|---|---|---|
|   | Composition (C5) | 25.00% |
|   | Dimethicone copolyol | 01.00% |
|   | Fragrance | 00.50% |
|   | Amonyl ™ 380BA | 11.00% |
|   | Kathon ™ CG | 0.08% |
| B | Polyquaternium ™ 10 | 00.30% |
|   | Lactic acid | qs |
|   | Water | qs 100% |
|   | Dye | qs |
|   | Lactic acid | qs pH 6 |

Procedure

Prepare separately phase B: mix until clear. Carefully mix in the ingredients in the indicated order.

C.12 Bath Powder

| A | Micropearl ™ M | 5.00% |
|---|---|---|
|   | Mica | 72.00% |
|   | Pigment | 3.00% |
| B | *Rosmarinus officinalis* (rosemary) leaf extract | 10.00% |
|   | Composition (C5) | 10.00% |

Procedure

Grind the powders of phase A. Dissolve the essential oil with composition 4 according to the invention (B) and slowly introduce this phase B into the ground material, leaving the mixture to stir for 6 minutes after the end of introduction of the liquid phase.

The characteristics of the products used in the preceding examples are as follows:

Sepitonic™ M3, a mixture of magnesium aspartate, zinc gluconate and copper gluconate, is an energizing active agent sold by the company SEPPIC.

Polyquaternium™ 10 is a quaternary ammonium salt of hydroxyethylcellulose, sold by the company Amerchol under the name Ucare Polymer™ JR-400.

Kathon™ CG, a mixture of methylchloroisothiazolinone and of methylisothiazolinone, is a preserving agent sold by the company Rohm & Haas.

Oronal™ LCG, a mixture of PEG-40 glyceryl cocoate and of sodium coceth sulfate, is a foaming agent sold by the company SEPPIC.

Amonyl™ 675SB is a cocamidopropyl hydroxy sultaine, sold by the company SEPPIC.

Sepicide™ HB, a mixture of phenoxyethanol, methyl paraben, ethyl paraben, propyl paraben and butyl paraben, is a preserving agent sold by the company SEPPIC.

Capigel™ 98 is an acrylate copolymer sold by the company SEPPIC.

Sepicide™ CI, imidazolineurea, is a preserving agent sold by the company SEPPIC.

Sepicide™ HB2, a mixture of phenoxyethanol, methyl paraben, ethyl paraben, propyl paraben, butyl paraben and isobutyl paraben, is a preserving agent sold by the company SEPPIC.

Proteol™ Oat is a mixture of N-lauryl amino acids obtained by total hydrolysis of oat protein as described in WO 94/26694 and sold by the company SEPPIC.

Montaline™ C40 is a salt of monoethanolamine cocamidopropyl betainamide chloride.

Montanov™ S (C12-C18 alcohols and cocoglucosides) is a self-emulsifying composition such as those described in EP 0 729 382, sold by the company SEPPIC.

Sepicap™ MP is a mixture of N-cocoyl amino acids and of the potassium salt of dimethicone PEG-7 panthenyl phosphate, sold by the company SEPPIC.

Aquaxyl™ is a moisturizing active agent comprising a mixture of xylitylpolyglucosides, anhydroxylitol and xylitol, sold by the company SEPPIC.

Somepon™ T25 is a sodium methyl cocoyl taurate, sold by the company SEPPIC.

Lipacide™ UGB is undecylenoyl lysine, sold by the company SEPPIC.

Oramide™ DL 200 AF is a diethanolamide cocamide sold by the company SEPPIC.

Amonyl™ 380BA is a cocamidopropyl betaine sold by the company SEPPIC.

Micropearl™ M is a crosslinked polymethyl methacrylate polymer in powder form, which is used as a texture modifier.

What is claimed is:

1. A method for improving the foaming properties of at least one of a cleansing or detergent formulation for topical use having at least one of a foaming or detergent surfactant, the method comprising: incorporating into said formulation an effective amount of a compound of formula (I):

$$R_1\text{—O-}(G)_x\text{-H} \qquad (I)$$

wherein,
x represents a decimal number between 1 and 5,
G represents a reducing sugar residue, and
$R_1$ represents a monovalent radical of formula (A):
—$CH_2$—$(CHOH)_n$—$CH_2$—OH (A), wherein n is an integer equal to 2, 3 or 4, or
$R_1$ represents a monovalent radical of formula (B):
—$(CH_2$—CHOH—$CH_2$—O$)_m$H (B), wherein m is an integer equal to 1, 2 or 3,
or a mixture of compounds of formula (I).

2. The method according to claim 1, wherein G represents a reducing sugar residue selected from the group consisting of: glucose, dextrose, sucrose, fructose, idose, gulose, galactose, maltose, isomaltose, maltotriose, lactose, cellobiose, mannose, ribose, xylose, arabinose, lyxose, allose, altrose, dextran and talose.

3. The method according to claim 1, wherein G represents a reducing sugar residue selected from the group consisting of: glucose, xylose and arabinose.

4. The method according to claim 1, wherein the at least one of a foaming or detergent surfactant is a compound of formula (II):

$$R_2\text{—}[O\text{—}(CH_2\text{—}CH_2\text{—}O)_p SO_3]_r X \qquad (II)$$

wherein,
$R_2$ represents a saturated or unsaturated, linear or branched aliphatic hydrocarbon-based radical containing from 6 to 22 carbon atoms,
p represents a decimal number between 1 and 10,
r is an integer equal to 1 or 2, and
X represents a cation of an alkali metal or of an alkaline-earth metal, ammonium ion, hydroxyethylammonium ion or tris(hydroxyethyl)ammonium ion,
or a mixture of compounds of formula (II).

5. The method according to claim 1, wherein the at least one of a foaming or detergent surfactant is a compound of formula (III):

$$R_3\text{—O—}(S)_y\text{—H} \qquad (III)$$

wherein,
y represents a decimal number between 1 and 5,
S represents a reducing sugar residue, and
$R_3$ represents a linear or branched, saturated or unsaturated alkyl radical containing from 8 to 16 carbon atoms.

6. The method according to claim 1, wherein a mass ratio of compound of formula (I) to foaming and/or detergent surfactant present in said formulation for topical use is between 1/30 and 10/1.

7. The method according to claim 4, wherein a mass ratio of compound of formula (I) to foaming and/or detergent surfactant present in said formulation for topical use is between 1/30 and 10/1.

8. The method according to claim 5, wherein the mass ratio of compound of formula (I) to foaming and/or detergent surfactant present in said formulation for topical use is between 1/30 and 10/1.

9. The method according to claim 4, wherein p represents a decimal number between 2 and 4.

10. The method according to claim 1, wherein x is a number between 1.05 and 2.

11. The method according to claim 1, wherein the effective amount of the compound of formula (I) is incorporated into the formulation in an amount of 0.1% to 20% by mass of total formulation.

12. The method according to claim 1, wherein the effective amount of the compound of formula (I) is incorporated into the formulation in an amount 1% to 5% by mass of total formulation.

13. The method according to claim 4, wherein X is sodium, magnesium or ammonium.

14. The method according to claim 5, wherein y is a number between 1.05 and 2.

15. The method according to claim 5, wherein $R_3$ is an n-octyl radical, n-decyl radical, n-dodecyl radical, n-tetradecyl radical or n-hexadecyl radical.

* * * * *